United States Patent [19]

Wilson et al.

[11] Patent Number: 4,610,878

[45] Date of Patent: Sep. 9, 1986

[54] USE OF IN VITRO ASSAY TECHNIQUES TO MEASURE PARAMETERS RELATED TO CLINICAL APPLICATIONS OF TRANSFER FACTOR THERAPY

[75] Inventors: Gregory B. Wilson, Mt. Pleasant; Herman H. Fudenberg, Isle of Palms, both of S.C.

[73] Assignee: Medical University of South Carolina, Charleston, S.C.

[21] Appl. No.: 504,986

[22] Filed: Jun. 16, 1983

[51] Int. Cl.[4] .................... A61K 35/14; A61K 39/00; C12Q 1/02

[52] U.S. Cl. ..................... 424/88; 424/101; 435/4; 435/29; 435/7; 436/811

[58] Field of Search ................ 436/519, 811, 63; 435/29, 7; 424/88, 101

[56] References Cited

U.S. PATENT DOCUMENTS 3,988,115 10/1976 Modabber ............................ 436/519
4,124,701 11/1978 Bach et al. .......................... 436/519
4,284,412 8/1981 Hansen et al. ...................... 436/519

OTHER PUBLICATIONS

Natelson et al—Clinical Immunochemistry (1978) (article by Fudenberg), pp. 228, 232, 233, 237–238, 241 and 248.
Wilson et al—Lymphokines, vol. 4 (1981), pp. 107–173.
Bach—Immunology (1982), pp. 376–378 (Pub. John Wiley).

Primary Examiner—Sam Rosen
Attorney, Agent, or Firm—Saidman, Sterne, Kessler & Goldstein

[57] ABSTRACT

Described herein are methods for quantifying in vitro various parameters related to the use of transfer factor (e.g., dialyzable leukocyte extract containing transfer factor) in the therapeutic and/or prophylactic treatment of patients having antigen-selective defects in cell mediated immunity, so as to standardize such parameters, predict or estimate therefrom the effectiveness of such treatment in vivo, determine optimum dosages and/or administrative regimens therefor and monitor the progress of patients receiving such treatment.

In one embodiment of the invention, the quantification of the various parameters is based upon in vitro assays which measure mediators of cellular immunity produced and released by appropriate leukocytes (e.g., those of the patient before treatment, those of potential donors, those of target cells, those of the patient after treatment with transfer factor, and the like) sensitized to a specific antigen. In another embodiment of the invention the in vitro assays employed are those which provide a measure of tumor-antigen specific cytotoxicity mediated by T cells, i.e., a measure of the increase in activity or number of cytotoxic T cells specific for tumor antigens.

22 Claims, 2 Drawing Figures

FIG.1

USE OF IN VITRO ASSAY TECHNIQUES TO MEASURE PARAMETERS RELATED TO CLINICAL APPLICATIONS OF TRANSFER FACTOR THERAPY

BACKGROUND OF THE INVENTION

The invention disclosed and claimed herein was made with support of the U.S. Government (NIH Grants R01 CA 25756 and R01 HD 09938) and is subject to certain government rights.

The present invention relates to the fields of immunotherapy and immunoprophylaxis and, more particularly, to the use in immunotherapy or immunoprophylaxis of transfer factor (e.g., dialyzable leukocyte extract containing transfer factor), and to in vitro assay techniques for the purposes of, inter alia, selecting appropriate donors for transfer factor preparations, determining transfer factor potency therein and predicting in vivo responses thereto.

In the mid-1950's, it was first reported that delayed-type cutaneous hypersensitivity (DTH) to tuberculin (PPD) or streptococcal M substance could be passively transferred using extracts of leukocytes obtained from skin-test positive, normal human donors to previously skin-test negative, normal human recipients. Lawrence, H. S. (1955) J. Clin. Invest. 34, 219; Lawrence, H. S. and Papperheimer, A. M., Jr. (1956) J. Exp. Med. 104, 321. In 1963, Lawrence, et al. claimed that dialysates of leukocyte extracts ("dialyzable leukocyte extracts" or DLE) were as effective in transferring DTH as were whole leukocyte extracts (Trans. Assoc. Am. Physicians, 76, 84 (1963)). The active component(s) of the DLE was at that time termed "transfer factor" (TF), and, believing TF to be the only biological activity present in DLE, the art tended to use the term "transfer factor" alone when referring to transfers produced by DLE. However, since it is now known that DLE contains several hundred chemical moieties, many of which are very active biologically, it is now recognized that use of the term "DLE containing TF activity" is a more accurate description.

Reported attempts to use DLE containing TF for immunotherapy and/or immunoprophylaxis increased dramatically beginning in the early 1970's when we and others first successfully used DLE to treat patients with genetically determined immunodeficiency disease and demonstrated that DLE could, in addition to transferring antigen-specific, delayed-type cutaneous reactivity, also confer (a) resistance to and prophylaxis against infection and (b) the ability to produce antigen-specific mediators of cellular immunity. Although DLE has been used to treat a variety of patients with inherited or acquired immunodeficiency diseases, neoplasia, and many infectious diseases of viral, fungal, protozoal or mycobacterial etiology, the success of clinical trials to date has been extremely variable, even for a single disease or syndrome.

One reason for the variable clinical results with DLE has been the lack of a rapid in vitro test suitable for selecting leukocyte donors, for evaluating the potency of TF in DLE preparations obtained from donor leukocytes, for predicting the response of a patient to immunotherapy with DLE and for determining the frequency and amount of DLE for immunotherapy or immunoprophylaxis. In the past, most investigators used only transfer of DTH (skin tests) in normal volunteers or patients, since this was the only accepted measurement of TF activity in DLE. However, in vivo skin test assays have many drawbacks: (a) In many disorders of infectious etiology, antigens suitable for in vivo skin testing are not available; (b) Systemic conversion of DTH reactivity requires relatively large amounts (several milliliters) of DLE; thus, extensive skin testing in normal healthy volunteers to document the presence of a given TF in the preparation of DLE is not cost-effective. An in vitro assay for TF in DLE would require at least 1000-fold less DLE for testing; and (c) Skin testing is neither quantitative nor particularly sensitive, and the in vivo response to DLE is too variable among the different recipients to allow for determining TF potency or for predicting how much DLE a given patient should receive.

In the past few years, the applicants have documented that assays which measure the production of mediators of cellular immunity, e.g., production of leukocyte migration inhibition factor (LIF) as measured by the agarose leukocyte migration inhibition (LMI) assay, can be employed as an in vitro test for detecting TF activity in DLE, a finding confirmed by two other groups of investigators. See, Wilson, G. B., and Fudenberg, H. H., Lymphokines 4, 107 (1981); Borkowsky, W., and Lawrence, H. S., J. Immunol. 123, 1741 (1979); Sirianni, M. C., et al., Clin. Immunol. Immunopathol. 14, 300 (1979). These findings led to the possibility, now set forth in the present invention, of actually quantifying various parameters related to TF therapy and prophylaxis by in vitro assay (e.g., to compare TF potencies of various preparations, to determine how much TF preparation should be given to a particular patient, to test patient's cells to determine whether antigen-specific responsiveness can be induced by particular TF preparations, and the like).

SUMMARY OF THE INVENTION

According to the present invention, in vitro assays which provide a measure of mediators of cellular immunity produced and released by leukocytes (lymphocytes, monocytes, macrophages) sensitized to a specific antigen, such as the leukocyte migration inhibition assay, are employed to (a) document antigen-selective defects in cell mediated immunity in patients; (b) select potential donors of fluids, tissues or cells from which TF (e.g., DLE containing TF) for use in immunotherapy and immunoprophylaxis can be attained; (c) quantify the potency of transfer factor in various preparations (e.g., DLE); (d) test a patient's cells for responsiveness to TF preparations (e.g., DLE containing transfer factor) and to predict therefrom in vivo responsiveness; (e) determine dosages and administrative regimens of TF preparations (e.g., DLE containing TF) for immunotherapy and immunoprophylaxis; and (f) monitor a patient's response to treatment with transfer factor.

The methods of the present invention materially enhance the attainment of consistent, improved, efficacious results of using transfer factor (e.g., DLE containing TF), and makes it possible to standardize TF preparations according to antigen-selectivity and potency so as to greatly increase the potential for achieving the uniformity and predictability required of such products or preparations.

According to a particular embodiment of the present invention, antigen-selective defects in cell mediated immunity in a patient are documented by in vitro assay techniques. In this method, leukocytes obtained from a patient are grown in vitro and assayed, in the presence of various antigens, to obtain, either directly or indirectly, a measure of the mediators of cellular immunity produced and released by the leukocytes in response to each particular antigen. By comparison of the obtained measures against predetermined or internal standards, antigens as to which the patient exhibits a defect (in whole or in part) in cell mediated immunity can be identified.

In another embodiment of the invention, potential donors of fluids, tissues or cells from which TF can be obtained (e.g., leukocytes for the preparation of DLE) can be selected by in vitro assay techniques. Thus, for example, where it is desired to produce DLE containing TF which would produce antigen-specific mediators of cellular immunity, leukocyte donors are selected on the basis of their responsiveness to the specific antigen. Leukocytes obtained from a variety of potential donors are grown in vitro in the presence of specific antigen and assayed to obtain a measure of production and release of mediators of cellular immunity. Comparison of the obtained measures to predetermined or standard values is then used to select those donors having potential as a source of DLE capable of transferring the ability to produce mediators of cellular immunity to the specific antigen.

According to another embodiment of the invention, a TF preparation (e.g., DLE containing TF) obtained from a suitable donor is quantitated as to its TF potency for specific antigen. Thus, for example, leukocytes previously determined to be non-responsive to specific antigen are cultured in vitro with specific antigen and with DLE, and there is obtained by assay a measure of mediators of cellular immunity produced and released by the leukocytes. This measure can be standardized against predetermined or internal controls to obtain a measure of TF "potency", i.e., a measure of the ability of the TF to transfer or confer the ability to produce antigen-specific mediators of cellular immunity.

In another method according to the invention, it can be determined by in vitro assay whether a TF-containing preparation (obtained from appropriate donors and of some quantified TF potency) will actually effect transfer of antigen-specific cell mediated immunity to the patient. Thus, for example, leukocytes from the patient are grown in vitro with DLE containing TF and specific antigen, and a measure of the production and release of mediators of cellular immunity as to the specific antigen is obtained by assay to indicate the degree of effectiveness of transfer. In the same way, optimum TF (e.g., DLE containing TF) dosages and administration regimens can be determined by growing the patient's leukocytes in the presence of antigen and varying quantities of DLE. Assayed measures of mediators of cellular immunity permit a correlation (e.g., a dose-response curve) from which minimum or optimum effective dosages can be determined.

Still another feature of the present invention is the ability to monitor the continued effectiveness of TF in a patient receiving treatment (e.g., with DLE containing TF) for therapy or prophylaxis by periodically assaying leukocytes obtained from the patient, in the presence of antigen, for a measure of the production and release of mdiators of cellular immunity.

As earlier noted, the in vitro assaying techniques useful in the present invention include those techniques which provide a measure, either directly or indirectly, of the production of mediators of cellular immunity by lymphocytes, macrophages, monocytes sensitized to specific antigen. While the leukocyte migration inhibition (LMI) assay is preferred in this regard (measuring leukocyte migration inhibitory factor—LIF), a number of other such assays may be employed. For example, there can be used a macrophage migration inhibition assay, active T cell assay, resynthesized lymphocyte SRBC receptor assay, antibody-dependent cell-mediated cytotoxicity inhibition assay, leukocyte adherence inhibition assay and resynthesized Fc receptor assay. Examples of these and other potentially useful in vitro assays are given in H. H. Fudenberg, et al., "Dialyzable Leukocyte Extracts (Transfer Factor)—A Review of Clinical Results And Immunological Methods For Donor Selection, Evaluation of Activities And Patient Monitoring", in "Thymus, Thymic Hormones and T Lymphocytes", p. 391 (Academic Press, N.Y. 1980); H. H. Fudenberg, et al., "Immunotherapy With Dialyzable Leukocyte Extracts And Studies Of Their Antigen-Specific (Transfer Factor) Activity", Proc. Virchow Pirquet Med. Soc., 34, 3–87 (1980); and K. Y. Tsang, et al., "Osterosarcoma-Specific Dialyzable Extracts: Prophylaxis Post-Surgery In An Animal Model Of Human Osteosarcoma", in Fourth International Transfer Factor Workshop, p. 156 (Academic press, 1983), all of which are incorporated herein by reference.

Regardless of the assay employed, the actual mechanism for measuring produced and released materials is not critical and can be either biological (e.g., using target cells or tissues), biochemical (e.g., activating metabolites of a cell) or immunologic (e.g., immunoassays employing antibodies, polyclonal or monoclonal, to the mediators in question).

In the present invention, "transfer factor" includes transfer factor obtained from any mammalian species (including birds), since it is known that antigen-specific cell mediated immunity can be transferred across species lines. See, e.g., G. B. Wilson, et al., "Bovine Dialyzable Lymph Node Extracts Have Antigen-Dependent And Antigen-Independent Effects On Human Cell Mediated Immunity In Vitro", Cell. Immunol., 47, 1–18 (1979); G. B. Wilson, et al., "Bovine 'Transfer Factor'; An Oligoribonucleopeptide Which Initiates Antigen-Specific Lymphocyte Responsiveness", Thymus, 4, 335–350 (1982); and G. B. Wilson, et al., "Transfer Of Cell-Mediated Immunity In Vitro To Human Lymphocytes Using Dialyzable Leukocyte Extracts From Immune Burros", in Fourth International Transfer Factor Workshop, p. 213 (Academic Press 1983).

In addition, the transfer factor (although generally illustrated throughout as a DLE containing transfer factor) can be obtained from any body fluid, tissues or cells of such species capable of providing TF, including the supernatant obtained in culturing immune cells in vitro. TF-containing preparation can be employed in crude or fractionated/purified form.

In the following more detailed description of this invention, a particular case report is presented of a patient having a specific disease in order to illustrate in detail the various applications of an in vitro assay (here, the LMI assay) to transfer factor (here, DLE containing TF) immunotherapy. As will be apparent to those skilled in the art, the techniques and methods hereinafter described for this particular case can be applied to a host of patients and diseases and can make use of assay techniques and transfer factor preparations other than those specified.

DESCRIPTION OF THE DRAWINGS

FIG. 1 represents the dose-response curve used to calculate the potency of PPD-F-specific TF in DLE preparation 2, described hereinafter. The $MI_A$ and $MI_B$ values indicate migration inhibition produced by DLE alone (quantifies non-specific adjuvant components in DLE) or DLE plus PPD-F (100 ug/ml) when incubated with peripheral blood leukocytes obtained from normal healthy subjects nonresponsive to PPD-F. Each point is the mean±SEM for three or more determinations using leukocytes from different donors. The % $D_B$ and potency were calculated as described hereinafter. The $MI_A$ and $MI_B$ values for DLE concentrations above 40 ul were obtained after concentrating the preparation five-fold. The number of TF potency units per milliliter was calculated by dividing 45 (ul) into 1000 (ul/ml).

FIG. 2 is a chart illustrating the patient's clinical response to immunotherapy with DLE containing TF specific for PPD-F. The migration index (MI) indicates the response of the patient's cells to PPD-F as determined by the leukocyte migration inhibition assay. An MI>0.85 indicates no significant response to PPD-F. IU in the Figure is international units (however, other units can be used, e.g., mls.). The results for sputum smears and cultures indicate the presence or absence of [*M. fortuitum* and the extent of growth, respectively.

DETAILED DESCRIPTION OF THE INVENTION

A. Patient

The patient had pulmonary fibrosis documented (over 10 years earlier) by lung biopsy. The patient had a flu-like illness, characterized by cough, malaise, and myalgias. During the following 6 months he gradually developed weight loss, weakness, and a cough productive of yellow sputum.

Chest roentgenograms showed extensive destruction of the right lung with alveolar and interstitial shadows present on both the right and left sides. Culture of the sputum produced a heavy growth of *M. fortuitum*. The patient was treated with standard antituberculosis drugs, to which he showed no response. After 4 months this therapy was stopped and the patient was reevaluated.

Chest roentgenograms at that time revealed increased alveolar and interstitial densities at both bases and pleural thickening on the right. A transbronchial lung biopsy showed caseating necrosis and grew *M. fortuitum* when cultured. The patient was started on amikacin with good clinical response within a month. After 6 months of intermittent therapy with amikacin, both drug resistance and drug toxicity developed and amikacin was discontinued. The patient was later readmitted with hemoptysis and easy fatiguability. Chest roentgenograms showed a large cavity with an air fluid level in the right mid-lung zone and a small cavity in the left lateral lung zone.

B. Materials and Methods For Use In Immunologic Evaluation

Preparation of dialyzable leukocyte extracts

DLE was prepared from the leukocytes of normal healthy volunteers with demonstrated reactivity to *M. fortuitum* (PPD-F) (shown by the direct agarose LMI assay as described in G. B. Wilson, et al., "Effects Of Dialyzable Leukocyte Extracts With Transfer Factor Activity On Leukocyte Migration In Vitro. I. Antigen-Dependent Inhibition And Antigen-Independent Inhibition And Enhancement Of Migration", J. Lab. Clin. Med., 93, 800–818 (1979)) as described previously. See Welch, T. M., et al. in "Transfer Factor: Basic Properties and Clinical Applications" (M. S. Ascher, et al., Eds.), p. 399, Academic Press, N.Y., 1976, incorporated herein by reference. Lyophilized dialysates of freeze-thawed leukocytes were reconstituted in pyrogen-free distilled water at a concentration equal to $5 \times 10^8$ mononuclear leukocyte (MNL) equivalents per milliliter. This concentration of DLE is equal to 5 international units (IU) of DLE. All preparations of DLE were determined to be sterile prior to use in vivo or in vitro.

Donors of target cells for evaluating DLE potency.

Normal healthy adult volunteers served as donors of target cells (peripheral blood leukocytes, PBL) for use in evaluating the potency of TF specific for PPD-F in the various preparations of DLE. All of these normal subjects were shown to be nonresponsive initially to PPD-F (migration indices>0.90 in response to PPD-F) by the LMI assay.

Leukocyte migration inhibition assay.

Cell-mediated immunity to Candida (Hollister-Stier, Berkeley, Calif.), SK-SD (streptokinase-streptodornase, Lederle, Pearl River, N.Y.), PPD-F (purified protein derivative from *Mycobacterium fortuitum*), PPD-S (purified protein derivative from *Mycobacterium tuberculosis*, Statens Serum Institute, Copenhagen, Denmark), mumps (Lilly, Berkeley, Calif.), dermatophytin (Hollister-Stier, Berkeley, Calif.), and PHA (Wellcome Research Laboratories, Beckenham, England) was evaluated by the direct LMI assay in accordance with procedures described in Wilson, G. B., et al., J. Lab. Clin. Med. 93, 800 (1979) and Kyong, C. U., et al., Amer. J. Med. 68, 955 (1980), incorporated herein by reference. PBL ($2.0 \times 10^8$ cells/ml) were incubated with medium only (control) or test substances (antigen or mitogen) at 37° C. in a humidified incubator gassed with 5% $CO_2$ in air, for 90 min when Candida, SK-SD, mumps, or dermatophytin was employed and for 60 min when PHA, PPD-F, or PPD-S was used. PHA was employed at either 5 or 1 ug/ml; Candida at a dilution of 1/10, 1/20, or 1/40; SK-SD at 8000:2000, 4000:1000, 800:200, or 400:100 units/ml; PPD-S or PPD-F at 100 ug/ml; mumps at a dilution of 1/5, 1/10, or 1/20; and dermatophytin at a dilution of 1/30 or 1/60. The optimal concentrations of PHA and all antigens had been determined previously as described in Metcalf, J. F., et al., Amer. J. Med. 71, 485 (1981) and Kyong, supra. Responsiveness to antigen or mitogen is expressed as a migration index (MI), where $$MI = \frac{\text{area of migration of neutrophils in presence of antigen or mitogen}}{\text{area of migration of neutrophils in medium only}}.$$

For the highest concentration of each test substance used, an MI less than 0.80 indicates responsiveness [induction of production of leukocyte migration inhibitory factor (LIF)] to PHA; an MI less than 0.85 indicates responsiveness to Candida, dermatophytin, PPD-S, or PPD-F; and an MI less than 0.90 indicates responsiveness to mumps or SK-SD.

Determination of TF potency in DLE.

The procedure for determining TF potency in DLE is briefly summarized below for the four preparations of DLE tested in this study. A detailed description of the procedure, as it relates to the detection of TF activity in DLE, has been published previously, Wilson, G. B., and Fudenberg, H. H., Lymphokines 4, 107 (1981), incorporated herein by reference. (a) Aliquots of target cells (PBL) from three or more normal donors nonresponsive to PPD-F by LMI (MI≧0.90) were incubated in either medium alone, medium plus PPD-F (100 ug/ml), DLE (at various concentrations) in medium, or DLE (at various concentrations) plus PPD-F in medium for 30 min at 37° C. in a humidified incubator gassed with 5% $CO_2$ in air, before neutrophil migration. (b) After neutrophil migration (6–18 hr), the effects of PPD-F alone, DLE alone, and DLE plus PPD-F were quantitated by determining three migration indices termed, respectively, the MI, $MI_A$, and $MI_B$. The $MI_A$ value quantitates antigen-independent (LIF-independent) LMI produced by non-TF components. $MI_A$ values ≦0.80 indicate significant antigen-independent effects. The $MI_B$ value quantitates antigen-dependent LMI induced by LIF released from T lymphocytes newly sensitized by TF in the presence of specific antigen. An $MI_B$ value <0.90 indicates meaningful antigen-dependent LMI. In this study all concentrations of DLE were evaluated using target cells from at least three donors, and each donor's cells were tested in three to six replicate cultures. The MI, $MI_A$, and $MI_B$ values given below are the mean±SEM for all determinations.

All four DLE preparations were initially tested over a concentration range of 1 to 50 ul DLE per 100-ul cell suspension to determine a "working range" of concentrations for evaluating their TF potency. When the proper working range of DLE preparation is determined, the highest concentrations of DLE should produce mild antigen-dependent LMI ($MI_A$ between 0.80 and 0.70), which should be accompanied by antigen-dependent specific LMI if an appropriate antigen is employed (i.e., PPD-F in this study). At intermediate concentrations of DLE, only antigen-dependent specific LMI should be produced, whereas at low or suboptimal concentrations of DLE only antigen-independent enhancement of migration ($MI_A > 1.10$) or no effect at all should be seen. The potency is determined by using the intermediate concentration range, where only antigen-dependent LMI is produced.

From our experience in testing many preparations of DLE made in our laboratory and provided by other investigators, we have noted three problems which are sometimes encountered: (a) the DLE may be too dilute, (b) it may promote marked enhancement of PMN migration over a wide range of concentrations, or (c) it may be too toxic or produce pronounced migration inhibition over a wide concentration range. To overcome the first problem we simply relyophilize the DLE to concentrate it as much as 5- to 20-fold, after which the three effects noted above are usually observed.

Enhancing activity may be present if the DLE is too dilute or if it contains too high a concentration of non-TF components (relative to TF) which can (a) promote antigen-independent enhancement of PMN migration or (b) inhibit or suppress the effects of TF. We have previously demonstrated both components in DLE, particularly in preparations obtained from "buffy coat" cells rich in platelets. In these cases, the crude DLE preparations may never demonstrate TF activity regardless of the concentrations tested in vitro, and the TF may need to be purified or the suppressor or inhibitor removed prior to determining TF potency (see below).

Preparations which are too toxic or produce pronounced antigen-independent LMI over a wide concentration may simply be diluted or, alternatively, an aliquot of the preparation may be fractionated by Sephadex G-25 chromatography to obtain TF free of components promoting antigen-independent LMI (this method or others can be used for the purification discussed above). The aliquot of partially purified TF may then be tested in vitro to determine the TF potency of crude DLE. The rest of the crude DLE preparation may then be used for immunotherapy, since the components producing antigen-independent LMI appear to be nonspecific immunopotentiators (adjuvants) which might be beneficial to the patient.

After the "working range" of each DLE preparation was determined, the % $D_B$ values were calculated from the $MI_A$ and $MI_B$ values obtained for the intermediate range of each dose-response curve. The % $D_B$ is the parameter actually used to quantitate the TF activity in DLE, where $$\%D_B = [1-(MI_B/MI_A)] \times 100.$$

Values greater than 15–20% are highly significant.

Figure 1:
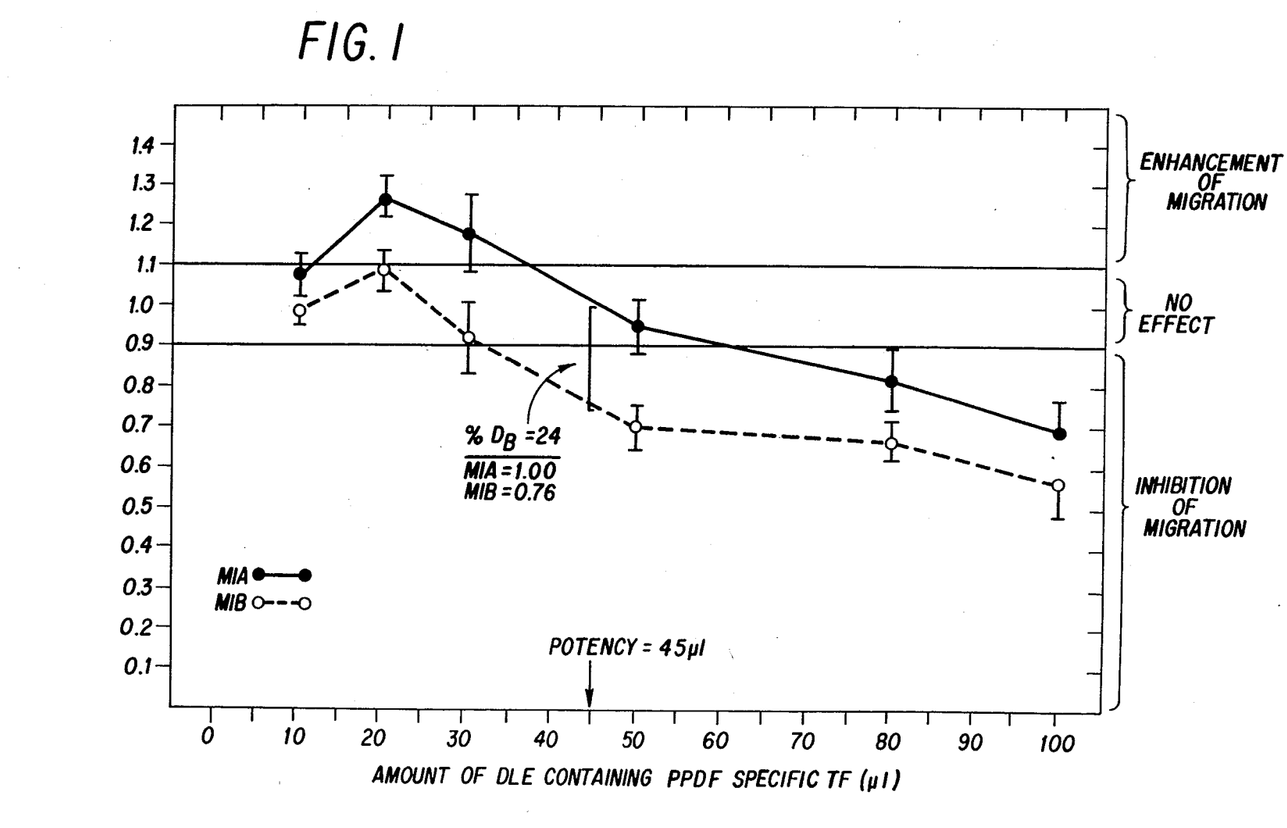

The TF potency of each DLE preparation was then determined (see FIG. 1). After determining the lowest concentration of DLE (microliters per 100-ul target cell suspension) which can produce a %$D_B$ of 20 while promoting an $MI_A$ value of ≧0.90 but <1.00, the potency units per milliliter DLE are quantitated by dividing this value into 1000 (The DLE is normally in 1.0 ml aliquots.). For example, if a preparation of DLE produces a %$D_B$ of 20 at 20 ul, then 1.0 ml of the preparation contains 50 potency units.

Determination of responsiveness of the patient's cells to DLE in vitro.

After each preparation of DLE was evaluated for TF potency in vitro using normal leukocytes, the ability of each preparation to convert the patient's cells to responsiveness to PPD-F in vitro was determined. In this phase of the study a protocol identical to that above was employed, except that evaluations with the patient's cells were restricted to testing each DLE preparation at concentrations known to produce %$D_B$ values of >15–20% when incubated with target cells from normal healthy controls (i.e., the intermediate concentration range of each dose—response curve was employed).

Estimation of Dosage of DLE for Immunotherapy.

Evaluation of representative DLE preparations used in our past clinical trials indicated that for DLE preparations containing 100 potency units per ml, 5 IU or 1.0 ml of DLE should be given. In the present study, we attempted to adhere closely to this ratio.

Other methods.

Active, inactive and total T cells, serum immunoglobulins, and PHA and concanavalin A (Con A)-induced lymphocyte DNA synthesis responses were determined, for the purpose of assessing the relative intactness of the patient's immune system, as described previously. See Metcalf, J. F., supra and Kyong, C. U., supra. See generally, H. H. Fudenberg, et al., "Dialyzable Leukocyte Extracts (Transfer Factor)—A Review Of Clinical Results And Immunological Methods For Donor Selection, Evaluation Of Activities And Patient Monitoring", in "Thymus, Thymic Hormones And T Lymphocytes", p. 391 (Academic Press, N.Y. 1980).

C. Results

Initial Evaluation of the Patient's Cell-Mediated Immunity.

After the patient was taken off amikacin therapy, immunologic evaluation indicated that he had seemingly intact cell-mediated immunity. Measurements of total white cells and lymphocytes were within normal limits and remained so throughout the period of study. Values for total T cells (range 63 to 80%) and active T cells (range 34 to 37%) were in the upper range of the normal levels of 68±8% and 25±6% (mean±SD), respectively. Serum immunoglobulins G, A, and M were also within normal limits. PHA- and Con A-induced lymphocyte DNA synthesis were low normal and normal, respectively, and remained unchanged throughout the study. In vitro testing with the LMI assay, however, suggested an antigen-selective defect in CMI for *M. fortuitum* (Table 1). The patient's cells responded to PHA, Candida, dermatophytin, mumps, SK-SD, and PPD-S, but not to PPD-F (MI=0.90). It was decided therefore to initiate immunotherapy with DLE containing TF specific for PPD-F.

Selection of Leukocyte Donors and Evaluation of TF Potency in Vitro.

Selection of potential leukocyte donors for DLE was based on demonstrated reactivity to PPD-F as shown by the LMI assay. Table 2 (second column) shows the MI value obtained for the normal healthy volunteers who provided cells for the preparation of DLE. Each lot of DLE was evaluated for PPD-F specific TF potency using target cells from normal subjects shown to be nonresponsive to PPD-F by LMI. The PPD-F-specific TF potency units per milliliter of each preparation are listed in Table 2, and FIG. 1 shows the entire dose—response curve or potency curve for DLE preparation 2.

Preparations 1 and 3 were too dilute when initially tested over a concentration range of 1 to 50 ul (both preparations produced enhancement of neutrophil migration at the highest concentration employed), and were therefore lyophilized, resuspended at five times their original concentrations, and retested. When DLE preparation 1 was retested, significant antigen-dependent LMI could not be demonstrated at any concentration. At high concentrations (>250 ul) preparation 1 produced pronounced migration inhibition, while at lower concentrations (10 to 80 ul) it enhanced neutrophil migration. Intermediate amounts of preparation 1 (90–200 ul) enhanced neutrophil migration in the presence of PPD-F over that seen without PPD-F ($MI_B > MI_A$) for target cells from some donors, and for others insignificant antigen-dependent LMI was obtained. These results suggested the presence of large amounts of components capable of inhibiting TF effects in DLE preparation 1. Based on these results, A TF potency of <5 units/ml was recorded for preparation 1, indicating that this preparation would probably have little or no therapeutic benefit.

When DLE preparation 3 was retested, its TF potency was calculated at 12.5 units/ml (Table 2). DLE preparation 2 (22.2 potency units per ml) was also concentrated after initial testing, primarily to obtain data for the "high dose" segment of the potency curve (FIG. 1). Preparation 4 (50 potency units per ml) did not require concentration.

Effects of DLE on the Patient's Clinical and Laboratory Parameters.

Figure 2:
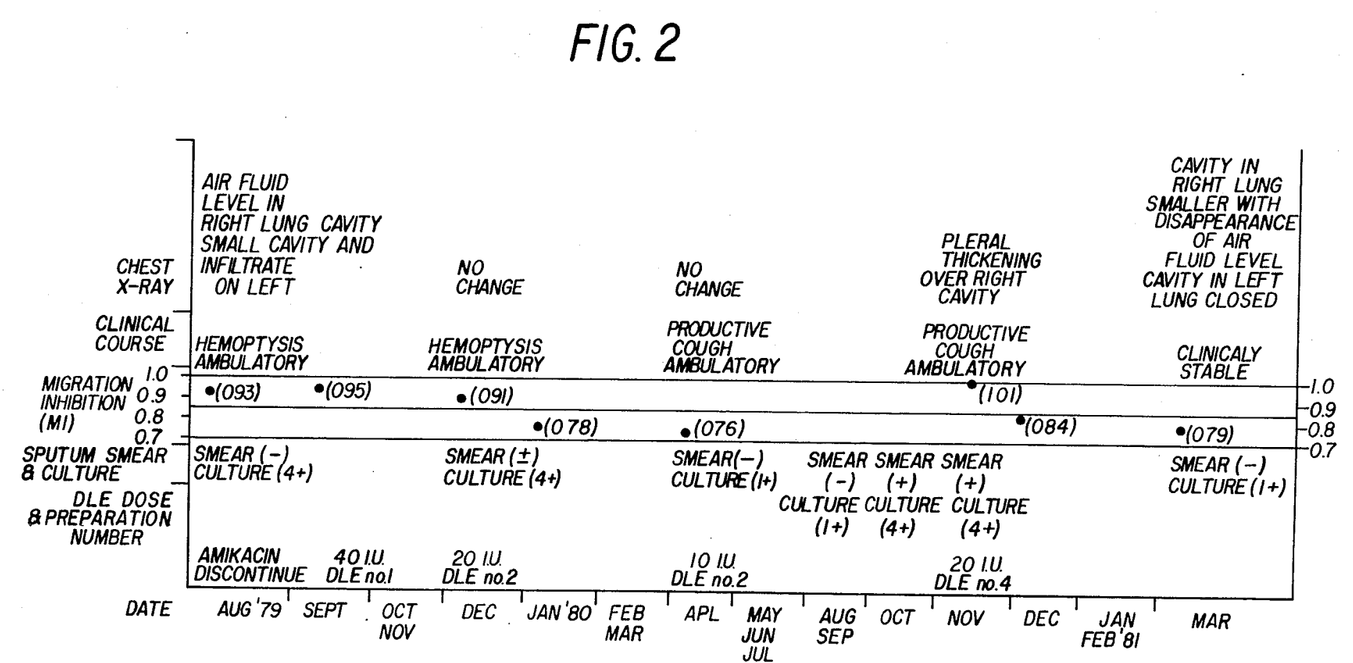

In September 1979 the patient was started on immunotherapy with DLE. FIG. 2 presents a summary of his clinical course for the period September 1979 to March 1981. Initially, 40 IU of DLE preparation 1 was administered; however, by December 1979 the patient's clinical condition had not improved and no response to PPD-F could be detected (MI=0.91). In December 1979 he was given 20 IU of DLE preparation 2; when

TABLE 1

PATIENT'S CELLULAR IMMUNE STATUS BEFORE IMMUNOTHERAPY AS SHOWN BY LEUKOCYTE MIGRATION INHIBITION ASSAY

| | Migration index (MI)[a] in presence of | | | | | | |
|---|---|---|---|---|---|---|---|
| | PHA | Candida | SK-SD | PPD-S | PPD-F | Mumps | Dermatophytin |
| Patient | 0.64 | 0.68 | 0.70 | 0.67 | 0.90 | 0.70 | 0.57 |
| Normal healthy controls[b] | 0.35–0.75 | 0.59–0.78 | 0.65–0.85 | 0.50–0.79 | 0.60–0.70 | 0.70–0.89 | 0.57–0.80 |

[a] MI, calculated as described under Materials and Methods. Concentrations used: PHA, 5 ug/ml; Candida 1:10; SK-SD, 8000:2000 units/ml; PPD-S, 100 ug/ml; PPD-F, 100 ug/ml; mumps, 1:5; dermatophytin, 1:30.
[b] Range of responses for normal healthy controls tested during same time period as the patient.

TABLE 2

EVALUATION OF DLE PREPARATIONS IN VITRO AND THE PATIENT'S RESPONSES IN VIVO AND IN VITRO

| DLE preparation | Donor's response to PPD-F[a] | In Vitro potency of DLE[b] | Recommended dosage of DLE for immunotherapy based on potency | | Response of patient's cells in vitro when incubated with DLE[d] | Dose of DLE used for therapy (IU)[c] | Response to *M. fortuitum* in vitro after DLE injection[e] |
|---|---|---|---|---|---|---|---|
| | | | IU[c] | ml | | | |
| 1 | 0.70 | <5 | >100 | 20.0 | No Response | 40 | No (inhibitor present?) |
| 2 | 0.61 | 22.2 | 22.5 | 4.5 | 28 | 20 | Yes |
| 3 | 0.55 | 12.5 | 40.0 | 8.0 | 21 | 30 | Yes |
| 4 | 0.68 | 50 | 10.0 | 2.0 | N.T. | 20 | Yes |

[a] MI value in response to PPD-F determined by leukocyte migration inhibition, MI <0.85 indicates response to PPD-F.
[b] TF potency units per milliliter DLE. Based on testing cells obtained from normal donors nonresponsive to *M. fortuitum* by leukocyte migration inhibition. TF potency as defined under Materials and Methods.
[c] International units. One IU is the material from $1 \times 10^8$ mononuclear cells, in a volume of 1.0 ml.
[d] % $D_B$ value (see Materials and Methods).
[e] See FIG. 2 for MI values in response to PPD-F after DLE therapy.

he was evaluated 3 weeks later (January 1980) he had developed a positive response to PPD-F in vitro and demonstrated clinical improvement (no hemoptysis, negative sputum smear). He received 10 IU of DLE preparation 2 on April 1980 and was stable clinically until October 1980, when his general clinical condition worsened. At that time his sputum smear was positive for *M. fortuitum* and no in vitro response to PPD-F could be detected by the LMI assay (FIG. 2). During this period we first evaluated the four preparations of DLE for PPD-F-specific potency. Based on our results (Table 2) the patient received 20 IU of DLE preparation 4 early in November 1980. Two weeks later his response to PPD-F had converted to positive when tested in vitro (FIG. 2).

Since November 1980 the patient has received prophylactic injections of DLE preparation 3 or preparation 4 every 4 to 6 months and has required no antituberculosis medication. Chest roentgenograms taken in March 1981 showed diminution of the major cavity with disappearance of the air fluid in the right lung and contraction and thickening of the pleura overlying the right lung. Also, the small cavity initially present in the left lung was no longer evident. A repeat transbronchial lung biopsy performed in April 1981 showed no caseation, in contrast to the overwhelming caseation present prior to the initiation of DLE therapy.

D. Discussion

*M. fortuitum* occurs widely in soil and is usually not considered a pathogen in man, since it rarely causes disease in healthy individuals. In a large series of patients with malignancy, however, *M. fortuitum* was the second most common cause of myobacterial disease. The patient described in this study seems to represent yet another instance in which *M. fortuitum* may cause serious disease, namely, when the patient's immune system is compromised due to an antigen-selective defect in CMI to the organism (Table 1).

We decided to institute immunotherapy with DLE containing TF specific for *M. fortuitum* for several reasons: (a) The patient had long-standing pulmonary fibrosis and a severe pulmonary parenchymal infection with *M. fortuitum,* which was refractory to treatment with standard antituberculosis medications and amikacin; (b) The patient appeared to have an antigen-selective defect in CMI to the infecting organism (Table 1); (c) Other than the selective defect to PPD-F, the patient's efferent CMI seemed relatively intact. (Past attempts to use DLE for immunotherapy have been particularly successful in patients with demonstrated antigen-selective defects in CMI but with efferent CMI responses otherwise intact); (d) DLE has been used as an immunotherapeutic agent with some degree of success (as judged by clinical improvement) in patients with disease resulting from infection with *M. tuberculosis, M. kansasil, M. intracellulare,* or *M. avium.*

When DLE preparations of known in vitro TF potency (Table 2) were used and therapeutic injections of DLE were administered in amounts commensurate with their TF potency, successful induction of responsiveness of PPD-F in vivo was obtained (FIG. 2). In addition, over the course of treatment, the patient has shown gradual clinical improvement (FIG. 2), his responsiveness to PPD-F has been maintained with prophylactic injections of DLE every 4–7 months (FIG. 2), and he has not required antituberculosis medications of any kind.

The predictive value of the LMI assay with respect to whether or not a patient will respond to TF (DLE) therapy is evident from the good correlation found in this study between the response to the patient's cells in vitro (Table 2) and his response to PPD-F after injections with DLE (FIG. 2). Preparations of DLE from different donors may differ markedly in their TF potency; for example, although all of our donors were selected on the basis of demonstrated responsiveness to PPD-F by LMI, the final TF potency of the preparations varied from 50 to less than 5 units/ml (Table 2). The LMI assay is of particular value here, since in treating out patient it was possible to gauge how much DLE should be administered for immunotherapy or immunoprophylaxis after the potency was determined. Finally, our results demonstrate that some preparations of DLE may be completely useless therapeutically even though the DLE donor has demonstrated CMI to the organism in question. Undoubtedly, many past clinical failures can be attributed to the use of DLE preparations with insufficient TF potency.

What is claimed is:

1. A method for quantifying parameters related to the clinical use of transfer factor and/or preparations containing transfer factor, said parameters listed in paragraphs, Ia–Ig below, said parameters being selected from the group consisting of:

(Ia) documentation of antigen-selective defects in cell-mediated immunity in patients;

(Ib) selection of potential donors of body fluids, tissues or cells for the making of preparations containing transfer factor;

(Ic) determination of the efficacy of transfer factor in preparations containing transfer factor;

(Id) determination of the responsiveness of the cells of a particular patient to preparations containing transfer factor;

(Ie) prediction of a particular patient's in vivo responsiveness to therapy and/or prophylaxis with preparations containing transfer factor;

(If) determination of dosages of, and administration frequency for, preparations containing transfer factor required for therapy and/or prophylaxis for a particular patient; and (Ig) the monitoring of a particular patient's responsiveness to treatment with preparations containing transfer factor;

said method comprising obtaining by means of in vitro assay techniques, a measure of mediators of cellular immunity produced and released by leukocytes, said leukocytes set out in paragraphs IIa–IIg below, said leukocytes selected from the group consisting of, for said correspondingly-referenced parameters Ia–Ig:

(IIa) leukocytes of a patient in response to a specific antigen:

(IIb) leukocytes of a potential donor in response to a specific antigen;

(IIc) leukocytes of a subject previously determined not to be responsive to a specific antigen, which leukocytes are newly-sensitized to said specific antigen with a preparation containing transfer factor;

(IId), (IIe), (IIf) leukocytes of a patient newly-sensitized to a specific antigen with a preparation containing transfer factor; and (IIg) leukocytes of a patient, who has been treated with a preparation containing transfer factor, in response to a specific antigen;

comparing and correlating said obtained measure of produced and released mediators of cellular immunity to a predetermined standard therefor, and determining the quantification of the parameters of Ia–Ig.

2. The method according to claim 1 wherein said preparation containing transfer factor is obtained from fluids, tissues or cells of any mammalian species.

3. The method according to claim 2 wherein said preparation containing transfer factor is dialyzable leukocyte extract containing transfer factor.

4. The method according to claim 1 wherein said in vitro assay technique measures the production and release of mediators of cellular immunity from said leukocytes by means selected from the group consisting of biological, biochemical and immunological means.

5. The method according to claim 1 wherein said in vitro assay technique is selected from the group consisting of macrophage migration inhibition assay, leukocyte migration inhibition assay, active T cel (rosette formation) assay, resynthesized lymphocyte SRBC receptor assay, leukocyte adherence inhibition assay, antibody-dependent cell-mediated cytotoxicity inhibition assay and resynthesized Fc receptor assay.

6. A method for quantifying parameters related to the clinical use of dialyzable leukocyte extracts containing transfer factor, said parameters set out in paragraphs Ia–Ig below, said parameters selected from the group consisting of:

(Ia) documentation of antigen-selective defects in cell mediated immunity in patients;

(Ib) selection of potential donors of leukocytes for the preparation of dialyzable leukocyte extracts containing transfer factor;

(Ic) determination of the efficacy of transfer factor in a dialyzable leukocyte extract containing transfer factor;

(Id) determination of the responsiveness of the cells of a particular patient to dialyzable leukocyte extract containing transfer factor;

(Ie) prediction of a particular patient's in vivo responsiveness to therapy with dialyzable leukocyte extract containing transfer factor;

(If) determination of dosages of, and administration frequency for, dialyzable leukocyte extract containing transfer factor required for therapy and/or prophylaxis for a particular patient; and (Ig) the monitoring of a particular patient's responsiveness to treatment with dialyzable leukocyte extract;

said method comprising obtaining, by means of in vitro assay techniques, a measure of mediators of cellular immunity released or produced from leukocytes, said leukocytes set out in paragraphs IIa–IIg below, said leukocytes selected from the group consisting of, for said correspondingly-referenced parameters Ia–Ig:

(IIa) leukocytes of a patient in response to a specific antigen;

(IIb) leukocytes of a potential donor in response to a specific antigen;

(IIc) leukocytes of a subject, previously determined not to be responsive to a specific antigen, which are newly-sensitized to said specific antigen with dialyzable leukocyte extract containing transfer factor;

(IId), (IIe), (IIf) leukocytes of a patient newly-sensitized to a specific antigen with dialyzable leukocyte extract containing transfer factor; and (IIg) leukocytes of a patient, who has been treated with dialyzable leukocyte extract containing transfer factor, in response to a specific antigen;

comparing and correlating said obtained measure of produced and released mediators of cellular immunity to a predetermined standard therefore; and determining the quantification of the parameters of Ia–Ig.

7. The method according to claim 6 wherein said in vitro assay technique measures the production and release of mediators of cellular immunity from said leukocytes by means selected from the group consisting of biological, biochemical and immunological means.

8. The method according to claim 6 wherein said in vitro assay technique is selected from the group consisting of macrophage migration inhibition assay, leukocyte migration inhibition assay, active T cell (rosette formation) assay, resynthesized lymphocyte SRBC receptor assay, leukocyte adherence inhibition assay, antibody-dependent cell-mediated cytotoxicity inhibition assay and resynthesized Fc receptor assay.

9. A method for selecting potential donors of leukocytes for the preparation of dialyzable leukocyte extract containing transfer factor for the in vivo treatment of a patient having a defect in cell mediated immunity for a specific antigen, comprising obtaining leukocytes from a potential donor, obtaining by in vitro assay a measure of mediators of cellular immunity released and produced by said leukocytes in response to said specific antigen, and comparing said obtained measure against a predetermined or internal standard indicative of the responsiveness of such leukocytes to specific antigen and of the potential ability of dialyzable leukocyte extract prepared from said donor to confer the ability to produce mediators of cellular immunity in response to said specific antigen in patients having a defect in cell mediated immunity therefor.

10. The method according to claim 9 wherein said in vitro assay technique measures the production and release of mediators of cellular immunity from said leukocytes by means selected from the group consisting of biological, biochemical and immunological means.

11. The method according to claim 9 wherein said in vitro assay technique is selected from the group consisting of macrophage migration inhibition assay, leukocyte migration inhibition assay, active T cell (rosette formation) assay, resynthesized lymphocyte SRBC receptor assay, leukocyte adherence inhibition assay, antibody-dependent cell-mediated cytotoxicity inhibition assay and resynthesized Fc receptor assay.

12. A method for quantifying the efficacy of transfer factor in a dialyzable leukocyte extract, comprising the steps of:

(a) obtaining from a subject leukocytes previously determined not to be responsive to a specific antigen;

(b) treating said leukocytes with dialyzable leukocyte extract in the presence of said specific antigen;

(c) obtaining by in vitro assay a measure of mediators of cellular immunity produced and released by said leukocytes; and (d) assigning to said dialyzable leukocyte extract a value correlated to said obtained measure and indicative of the relative ability of said dialyzable leukocyte extract to transfer or confer, in leukocytes previously non-responsive to said specific antigen, the ability to produce mediators of cellular immunity in response to said specific antigen.

13. The method according to claim 12 wherein said in vitro assay technique measures the production and release of mediators of cellular immunity from said leukocytes by means selected from the group consisting of biological, biochemical and immunological means.

14. The method according to claim 12 wherein said in vitro assay technique is selected from the group consisting of macrophage migration inhibition assay, leukocyte migration inhibition assay, active T cell (rosette formation) assay, resynthesized lymphocyte SRBC receptor assay, leukocyte adherence inhibition assay, antibody-dependent cell-mediated cytotoxicity inhibition assay and resynthesized Fc receptor assay.

15. A method for predicting the effectiveness of in vivo treatment of a particular patient with dialyzable leukocyte extract containing transfer factor, comprising:
(a) obtaining leukocytes from said patient having a previously documented defect in cell mediated immunity for a specific antigen;
(b) treating said leukocytes with a dialyzable leukocyte extract containing transfer factor in the presence of said specific antigen;
(c) obtaining by in vitro assay a measure of mediators of cellular immunity produced and released by said leukocytes; and
(d) comparing said obtained measure to a predetermined standard indicative of the effectiveness of said dialyzable leukocyte extract to transfer or confer to the leukocytes of said patient in vivo the ability to produce mediators of cellular immunity in response to said specific antigen.

16. The method according to claim 15 wherein said in vitro assay technique measures the production and release of mediators of cellular immunity from said leukocytes by means selected from the group consisting of biological, biochemical and immunological means.

17. The method according to claim 15 wherein said in vitro assay technique is selected from the group consisting of macrophage migration inhibition assay, leukocyte migration inhibition assay, active T cell (rosette formation) assay, resynthesized lymphocyte SRBC receptor assay, leukocyte adherence inhibition assay, antibody-dependent cell-mediated cytotoxicity inhibition assay and resynthesized Fc receptor assay.

18. A method for determining the dosages and administration regimen of a particular dialyzable leukocyte extract containing transfer factor effective to confer in vivo, in a particular patient, the ability to produce mediators of cellular immunity in response to a specific antigen, comprising the steps of:
(a) obtaining a dialyzable leukocyte extract containing transfer factor, said extract having a previously quantified ability, with respect to leukocytes other than those of the particular patient, to transfer or confer to such leukocytes in vitro the ability to produce mediators of cellular immunity in response to said specific antigen;
(b) obtaining a population of leukocytes from said patient;
(c) treating sub-populations of said leukocytes from said patient with varying quantities of said dialyzable leykocyte extract in the presence of said specific antigen;
(d) obtaining a measure, by in vitro assay, of mediators of cellular immunity produced and released by each such sub-population so as to thereby obtain a correlation of various dosages of said dialyzable leukocyte extract and their effectiveness for a particular patient.

19. The method according to claim 18 wherein said in vitro assay technique measures the production and release of mediators of cellular immunity from said leukocytes by means selected from the group consisting of biological, biochemical and immunological means.

20. The method according to claim 18 wherein said in vitro assay technique is selected from the group consisting of macrophage migration inhibition assay, leukocyte migration inhibition assay, active T cell (rosette formation) assay, resynthesized lymphocyte SRBC receptor assay, leukocyte adherence inhibition assay, antibody-dependent cell-mediated cytotoxicity inhibition assay and resynthesized Fc receptor assay.

21. A methodology for the therapeutic and/or prophylactic use of dialyzable leukocyte extracts containing transfer factor for patients having defects in cell mediated immunity with respect to a specific antigen, comprising the steps of:
(a) documenting antigen-selective defects in cell mediated immunity in a patient by obtaining leukocytes from a patient, maintaining said leukocytes in vitro in the presence of a specific antigen, obtaining a measure, by in vitro assay, of the production and release from said leukocytes of mediators of cellular immunity and utilizing said obtained measure to identify a specific antigen as to which a defect in cell mediated immunity thereto is exhibited by the patient;
(b) selecting potential donors of leukocytes for the preparation of dialyzable leukocyte extract containing transfer factor for use in treatment of the antigen-selective defect identified in (a) by obtaining leukocytes from a donor, maintaining said leukocytes in vitro in the presence of the specific antigen identified in (a), and obtaining a measure, by in vitro assay, of the production and release of mediators of cellular immunity by such leukocytes in response to such antigen, so as to thereby identify a donor exhibiting production and release of mediators of cellular immunity with respect to the antigen;
(c) preparing dialyzable leukocyte extract from the donor;
(d) quantifying the potency of transfer factor in said dialyzable leukocyte extract by identifying a subject who is not responsive to said antigen, obtaining leukocytes from said subject, maintaining said leukocytes in vitro in the presence of said antigen and said dialyzable leukocyte extract, and obtaining a measure, by in vitro assay, of the production and release by such leukocytes of mediators of cellular immunity with respect to the antigen, so as to thereby assign a value to said dialyzable leukocyte extract indicative of its capability of transferring the ability to produce and release mediators of cellular immunity;
(e) preparing a dosage/response correlation between said dialyzable leukocyte extract and leukocytes of the patient by obtaining leukocytes from the patient, maintaining sub-populations of said leukocytes in vitro in the presence of the specific antigen and varying quantities of said dialyzable leukocyte extract, and obtaining a measure for each such quantity of the production and release of mediators of cellular immunity with respect to the specific antigen; and (f) administering to the patient a quantity of said dialyzable leukocyte extract determined in (e) to be effective in transferring to leukocytes of the patient the ability to produce and release mediators of cellular immunity with respect to the specific antigen.

22. A method for quantifying parameters related to the clinical use of transfer factor and/or preparations containing transfer factor, said parameters set out in paragraphs Ia–Ig below, said parameters being selected from the group consisting of:

(Ia) documentation of antigen-selective defects in cell-mediated immunity in patients;

(Ib) selection of potential donors of body fluids, tissues or cells for the making of preparations containing transfer factor;

(Ic) determination of the efficacy of transfer factor in preparations containing transfer factor;

(Id) determination of the responsiveness of the cells of a particular patient to preparations containing transfer factor;

(Ie) prediction of a particular patient's in vivo responsiveness to therapy and/or prophylaxis with preparations containing transfer factor;

(If) determination of dosages of, and administration frequency for, preparations containing transfer factor required for therapy and/or prophylaxis for a particular patient; and (Ig) the monitoring of a particular patient's responsiveness to treatment with preparations containing transfer factor;

said method comprising obtaining, by means of in vitro assay techniques, a measure of the T cell mediated, tumor antigen-specific cytotoxicity exhibited by cells of the patient, donor or other appropriate target cells, in the presence of antigen and, where applicable, in the presence of said transfer factor preparation, and determining the quantification of the parameters of Ia–Ig.

* * * * *